United States Patent [19]

Kojima et al.

[11] 4,093,810

[45] June 6, 1978

[54] PROCESS FOR PRODUCING 4-CARBOXAMIDO-5-CYANO-2-IMIDAZOLONE

[75] Inventors: Takakazu Kojima, Yamato; Yozo Ohtsuka, Sagamihara, both of Japan

[73] Assignee: Sagami Chemical Research Center, Tokyo, Japan

[21] Appl. No.: 708,974

[22] Filed: July 26, 1976

[30] Foreign Application Priority Data

Jul. 25, 1975 Japan .................................. 50-90211

[51] Int. Cl.$^2$ .......................................... C07D 233/90
[52] U.S. Cl. .................................................. 548/321
[58] Field of Search ....................... 260/309.6; 548/321

[56] References Cited

U.S. PATENT DOCUMENTS 2,535,006  12/1950  Woodward ....................... 260/309.6
3,868,386  2/1975  Sanchez et al. ................... 260/309.6

FOREIGN PATENT DOCUMENTS 936,664  9/1963  United Kingdom .............. 260/309.5

OTHER PUBLICATIONS

Parker In:Raphael et al., Advances in Organic Chemistry Methods and Results, vol. 5, pp. 2–5, N.Y., Interscience-Wiley, 1965.

Primary Examiner—Natalie Trousof
Attorney, Agent, or Firm—Sughrue, Rothwell, Mion, Zinn and Macpeak

[57] ABSTRACT

A process for producing 4-carboxamido-5-cyano-2-imidazolone which comprises reacting diaminomaleonitrile with carbon dioxide in a polar solvent, optionally in the presence of a basic catalyst.

2 Claims, No Drawings

PROCESS FOR PRODUCING 4-CARBOXAMIDO-5-CYANO-2-IMIDAZOLONE

BACKGROUND OF THE INVENTION

1. Field of the Invention

This invention relates to a process for producing 4-carboxamido-5-cyano-2-imidazolone represented by the formula

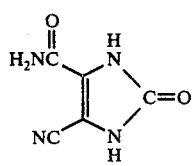

More particularly, this invention relates to an improved process for producing 4-carboxamido-5-cyano-2-imidazolone which comprises reacting diaminomaleonitrile (hereinafter referred to as DAMN) with carbon dioxide in a polar solvent, optionally in the presence of a basic catalyst.

2. Description of the Prior Art

4-Carboxamido-5-cyano-2-imidazolone obtained by the process of this invention has been known to be useful as a plant browth regulating agent, for example, for reducing the germination time of pea seeds and as an intermediate for the preparation of various pharmaceutical and agricultural agents, for example, uric acid, as described in R. A. Sanchez et al., U.S. Pat. No. 3,868,386. Further, 4-carboxamido-5-cyano-2-imidazolone can be converted into resins which are useful as textile crease and shrink-proofing agents, as described in U.S. Pat. No. 3,868,386.

Hitherto, a process for producing 4-carboxamido-5-cyano-2-imidazolone comprising a reaction between DAMN and a water-soluble bicarbonate salt such as ammonium bicarbonate, potassium bicarbonate, sodium bicarbonate, etc., in aqueous alkaline media has been disclosed in, for example, U.S. Pat. No. 3,868,386. However, the above conventional process is not considered to be an advantageous process, in particular, from the industrial standpoint, since the solvent used in the process is limited to only water. That is, a polar solvent solution of DAMN obtainable from a manufacturing step of DAMN cannot be used directly in the process for producing 4-carboxamido-5-cyano-2-imidazolone taught in the above prior art, and in addition, the use of an aqueous solution of DAMN is not advantageous due to the fact that the solubility of DAMN in water is low (about 0.6% at room temperature) and that the aqueous solution of DAMN tends to form a tar-like polymer due to the polymerization of HCN during the storage of the solution for a prolonged period of time.

DETAILED DESCRIPTION OF THE INVENTION

As a result of extensive study on a process for producing 4-carboxamido-5-cyano-2-imidazolone which can be used advantageously on an industrial scale, it was found that the above compound can be obtained easily in high yield by reacting DAMN with carbon dioxide in a polar solvent, optionally in the presence of a basic catalyst.

At present, the accumulation of carbon dioxide in the air due to the rapid consumption of a large amount of organic materials in industry in recent years has been one of serious problems from the standpoint of ambient pollutions and thus the conversion of carbon dioxide into useful organic materials has become one of important social requirements as a means of recovering carbon dioxide. In view of the above fact, the process of this invention is advantageous in converting carbon dioxide into useful organic compounds, particularly in fixing carbon dioxide as an organic compound having C-N bonds.

The starting material DAMN is well known in the art, for example, as disclosed in U.S. Pat. No. 3,701,797 and can easily be prepared from hydrogen cyanide.

In carrying out the process of this invention, the starting material DAMN is dissolved in a polar solvent. The concentration of DAMN in a polar solvent is not critical and can vary depending upon the type of the polar solvent used and, partly, upon the reaction temperature used. Generally, any concentration less than the maximum solubility of DAMN in the specific polar solvent at the specific reaction temperature employed in the reaction can be used, but use of too low concentrations of DAMN in the polar solvent would not be preferred from the economical standpoint since it requires a large volume of polar solvents. For example, 1 g of DAMN can be dissolved at room temperature in more than about 3 ml of dimethyl sulfoxide which is a typical example of the polar solvent used in the present invention.

Examples of polar solvents which can be used in the present invention are dimethyl sulfoxide (DMSO), N,N-dimethylformamide (DMF), alcohols having 1 to 4 carbon atoms such as methanol, ethanol, n-propanol, iso-propanol, n-butanol, sec-butanol, tert-butanol, etc., ethers such as tetrahydrofuran, dioxane, diethyl ether, dimethoxyethane, etc., pyridine, acetonitrile, ethyl acetate and the like. Of these solvents, dimethyl sulfoxide and N,N-dimethylformamide are preferred since they can form complexes (solvate compounds) with 4-carboxamido-5-cyano-2-imidazolone as a precipitate which can be conveniently purified by recrystallization before isolating the desired 4-carboxamido-5-cyano-2-imidazolone, as described hereinafter in detail.

The reaction between DAMN in a polar solvent and carbon dioxide can be conveniently achieved by a conventional technique, for example, by bubbling or blowing a carbon dioxide gas in the solution of DAMN, preferably with stirring. Alternatively, solid carbon dioxide (dry ice) can be used as a $CO_2$ source preferably in such a manner that dry ice is not directly contacted with the reaction mixture. Generally, the reaction proceeds smoothly at a temperature of from about 0° C to about 60° C, preferably at a temperature of from room temperature (about 20° – 30° C) to about 40° C, while blowing a carbon dioxide gas into the solution of DAMN in a polar solvent or adding a predetermined amount of dry ice, preferably contained in a separate vessel, to a solution of DAMN in a polar solvent. However, it should be noted that the reaction can also be carried out at a temperature outside the above range, for example, at a temperature below about 0° C in such an instance that dry ice is used or one desires to dissolve a large amount of carbon dioxide in a polar solvent to ensure a smooth reaction (the lower the reaction temperature, the higher is the solubility of carbon dioxide in a polar solvent).

The reaction can be carried out under atmospheric pressure or under pressurized conditions (autogeneous pressure) in either open vessels or closed vessels. Also, the reaction in a closed vessel can be carried out under either atmospheric pressure or autogeneous pressure which varies with the amount of carbon dioxide used but is generally about 2 to about 3 atms.

As is apparent to one skilled in the art, the reaction of DAMN and carbon dioxide to form 4-carboxamido-5-cyano-2-imidazolone requires theoretically an equimolar amount of reactants and, therefore, the amount of carbon dioxide required in the reaction can easily be determined from the amount of DAMN used. However, carbon dioxide is preferably used in an excess amount relative to the amount of DAMN to ensure that all the reactant DAMN used in the reaction is converted into 4-carboxamido-5-cyano-2-imidazolone. Generally, about 2 to 6 moles of carbon dioxide per mole of DAMN is sufficient in a closed vessel reaction. When carbon dioxide gas is blown or bubbled in an open vessel reaction, the rate of blowing or bubbling can freely be varied depending upon the scale of the reaction, the concentration of DAMN in the polar solvent, etc. In a small scale laboratory reaction, for example, carbon dioxide gas can be blown at a rate of about 3 ml/minute.

In an alternative procedure, the reaction between DAMN and carbon dioxide can be advantageously carried out in the presence of a basic catalyst. The use of the basic catalyst is not essential, but is preferred in order to ensure a smooth reaction between DAMN and carbon dioxide thereby shortening the reaction time and increasing the yield of the desired compound.

Examples of basic catalysts which can be used in the process of this invention are tertiary amines such as trialkylamines having 1 to 4 carbon atoms in each of the alkyl moieties thereof such as trimethylamine, triethylamine, etc., triethylenediamine, hexamethylenetetramine, N-methylmorpholine, pyridine, and the like, basic inorganic salts such as sodium cyanide and the like, and ammonia such as aqueous ammonia, for example, about 28% to 30% aqeuous ammonia which can be commercially available, etc. As is apparent from the foregoing, pyridine serves as both the polar solvent and the basic catalyst.

The basic catalyst can be used in an amount of from about 0.1 to about 1 mole per mole of DAMN.

The reaction system is not necessarily anhydrous and a small amount of water contained in alcohols as polar solvents and in aqueous ammonia as basic catalysts generally does not adversely affect the reaction between DAMN and carbon dioxide.

In the process of this invention, carbon dioxide is not necessarily pure $CO_2$ and any exhaust gas containing a substantial amount of $CO_2$ may also be used. However, from the industrial standpoint, a substantially pure carbon dioxide is advantageously used.

The time required for completing the reaction varies mainly depending upon the reaction temperature, i.e., the temperature of the solution of DAMN in a polar solvent, the concentration of the DAMN in a polar solvent, the blowing rate of carbon dioxide gas as well as the type of polar solvents used and the presence or absence of catalysts, etc., but generally the reaction can be continued until no appreciable amount of unreacted DAMN remains in the reaction mixture. The reaction can be terminated when no further precipitation of the product occurs in the reaction system. Generally, a reaction time of about 2 to about 100 hours would be sufficient in most instances.

4-Carboxamido-5-cyano-2-imidazolone produced by the process of this invention can form a complex or solvate with the solvent used and also can form a salt with a base used as a basic catalyst in the reaction and the present invention also includes within its scope a process for producing such complexes and salts. Free 4-carboxamido-5-cyano-2-imidazolone can easily be obtained from the above complex by merely recrystallizing the complex from water. Similarly, free 4-carboxamido-5-cyano-2-imidazolone can be obtained from the salt by recrystallizing the salt from water which preferably contains an acid in an amount sufficient to neutralize the base. However, the acid is not necessarily required for obtaining free 4-carboxamido-5-cyano-2-imidazolone, in particular, from a salt with a trialkylamine. Examples of acids which can be used for this purpose are inorganic acids such as hydrochloric acid, sulfuric acid and the like.

When a basic catalyst is used in the process of this invention, either a polar solvent or a base having a higher affinity to 4-carboxamido-5-cyano-2-imidazolone can form a complex or a salt, respectively. For example, dimethyl sulfoxide has an affinity higher than triethylamine and, thus, the product obtained from a reaction mixture containing dimethyl sulfoxide and triethylamine is generally a complex with dimethyl sulfoxide rather than a salt with triethylamine.

The present invention is further illustrated by the following Examples, but they are not to be construed as limiting the scope of this invention. Unless otherwise indicated, all percentages used therein are by weight.

EXAMPLE 1

10.8 g of diaminomaleonitrile and 10.1 g of triethylamine were dissolved in 150 ml of N,N-dimethylformamide and carbon dioxide gas was then blown into the solution at a rate of about 3 ml to 30 ml/minute while maintaining the solution at a temperature of 0° C for 1 hour and then at a temperature of 40° C for 38 hours. After completion of the reaction, 300 ml of diethyl ether was added to the reaction mixture, and 22.1 g of a precipitate of a complex of 4-carboxamido-5-cyano-2-imidazolone and N,N-dimethylformamide was separated by filtration. The complex thus obtained was found to decompose at a temperature higher than 250° C.

Elementary Analysis: Calcd. for $C_8H_{11}N_5O_3$: C, 42.67; H, 4.92; N, 31.10%. Found: C, 42.53; H, 4.85; N, 31.00%.

NMR Spectrum (DMSO-$d_6$)δ: 11.25 (bs, 2H), 7.97 (s, 1H), 7.60 (bs, 2H), 2.90 (s, 3H), 2.73 (s, 3H).

IR Absorption Spectrum (Nujol) $cm^{-1}$: 3375, 3150, 2240, 1720, 1660, 1610, 1462, 1410, 1104, 1017, 816, 747, 707.

The complex thus obtained was then recrystallized from water to give 14.8 g (98% yield) of 4-carboxamido-5-cyano-2-imidazolone as white crystals. The product was found to decompose at a temperature higher than 300° C.

Elementary Analysis: Calcd. for $C_5H_4N_4O_2$: C, 39.48; H, 2,65; N, 36.83%. Found: C, 39.38; H, 2.66; N, 36.88%.

The IR, UV and NMR absorption spectra of 4-carboxamido-5-cyano-2-imidazolone thus obtained were found to be quite consistent with those of an authentic sample disclosed in U.S. Pat. No. 3,868,386.

EXAMPLE 2

10.8 g of diaminomaleonitrile and 10.1 g of triethylamine were dissolved in 100 ml of dimethyl sulfoxide and the solution was stirred at room temperature for 22 hours while blowing carbon dioxide gas. 20 ml of ethanol and 300 ml of diethyl ether were then added to the reaction mixture to obtain 23.0 g (100% yield) of a 1:1 complex of 4-carboxamido-5-cyano-2-imidazolone and dimethyl sulfoxide. The product thus obtained was then recrystallized from dimethyl sulfoxide and ethanol and found to decompose at a temperature near 200° C.

Elemental Analysis: Calcd. for $C_7H_{10}N_4O_3S$: C, 36.52; H, 4.38; N, 24.33; S, 13.93%. Found: C, 36.62; H, 4.44; N, 24.48; S, 14.15%.

The complex obtained above was recrystallized from water to give 13.6 g (89% yield) of 4-carboxamido-5-cyano-2-imidazolone.

EXAMPLE 3

10.8 g of diaminomaleonitrile and 1.0 g of triethylamine were dissolved in 100 ml of dimethyl sulfoxide and the resulting solution was stirred at a temperature of 40° C for 22 hours while blowing carbon dioxide gas into the solution. The resulting reaction mixture was then worked up in the same manner as described in Example 2 to obtain 15.8 g (69% yield) of a 1:1 complex of 4-carboxamido-5-cyano-2-imidazolone and dimethyl sulfoxide. Recrystallization of the complex thus obtained from water gave 4-carboxamido-5-cyano-2-imidazolone.

EXAMPLE 4

10.8 g of diaminomaleonitrile and 0.49 g of sodium cyanide were dissolved in 100 ml of dimethyl sulfoxide and the resulting solution was stirred at room temperature for 22 hours while blowing carbon dioxide gas into the solution. The reaction mixture was then worked up in the same manner as described in Example 2 and the precipitate formed was washed with a small amount of ethanol to obtain 21.6 g (94% yield) of a 1:1 complex of 4-carboxamido-5-cyano-2-imidazolone and dimethyl sulfoxide.

Recrystallization of the complex thus obtained from water gave 4-carboxamido-5-cyano-2-imidazolone.

EXAMPLES 5 to 10

10.8 g of diaminomaleonitrile was reacted with carbon dioxide gas using each of the solvents and the bases indicated in Table below under the reaction conditions also indicated in Table below. In each instance, 4-carboxamido-5-cyano-2-imidazolone or a complex or salt thereof was obtained in the yield shown in Table.

The triethylamine salt of 4-carboxamido-5-cyano-2-imidazolone obtained in this example was found to turn into a red-brown colored product at a temperature higher than 190° C and decomposed at a temperature higher than 250° C. This complex had the following characteristics.

NMR Spectrum (DMSO-$d_6$)δ: 8.2 (2H), 7.5 (2H), 2.68 (q, J=7Hz, 6H), 1.03 (t, J=7Hz, 9H).

IR Absorption Spectrum (KBr disc) cm$^{-1}$: 3450, 3220, 2670, 2235, 1720, 1602, 1445, 1300, 1030, 750, 703.

Table

| Example | Polar Solvent | Basic Catalyst | Reaction Temp. (° C) | Reaction Time (hrs.) | Product | Yield (%) |
| --- | --- | --- | --- | --- | --- | --- |
| 5 | Acetonitrile (200 ml) | Triethylamine (10.1 g) | 40 | 20 | Triethylamine Salt of CCI* | 90 |
| 6 | Pyridine (100 ml) | — | 40 | 43 | CCI | 74 |
| 7 | Ethanol (150 ml) | Triethylamine (10.1 g) | 40 | 18 | DMSO Complex of CCI | 70 |
| 8 | Dimethyl Sulfoxide (100 ml) | 28% Aq. Ammonia (5.5 g) | 40 | 22 | DMSO Complex of CCI | 95 |
| 9 | Tetrahydrofuran (200 ml) | Triethylamine (10.1 g) | 0 | 5 | Triethylamine Salt of CCI | 51 |
| 10 | Dimethyl Sulfoxide (100 ml) | — | 40 | 67 | DMSO Complex of CCI | 16 |

*CCI = 4-carboxamido-5-cyano-2-imidazolone

EXAMPLE 11

30 ml of acetonitrile and 0.310 g (3.06 m moles) of triethylamine were charged into a 200 ml-round bottle flask equipped with a 250 ml-gas buret and the reaction system was purged with a carbon dioxide gas under atmospheric pressure. 0.330 g (3.15 m moles) of diaminomaleonitrile was then added to the reaction system and a $CO_2$ absorption rate was determined by the gas buret while stirring and found that 39%, 66% and 90% of $CO_2$ gas charged had been absorbed 36 minutes, 90 minutes and 233 minutes, respectively, after initiation of the reaction. Then, about 100 ml of diethyl ether was added to the reaction mixture to obtain 0.650 g (82% yield) of a salt of 4-carboxamido-5-cyano-2-imidazolone and triethylamine as a precipitate. The salt thus obtained was dissolved in dimethyl sulfoxide and diethyl ether was added to the resulting solution to precipitate 0.570 g (74% yield) of a complex of 4-carboxamido-5-cyano-2-imidazolone and dimethyl sulfoxide.

Recrystallization of the complex thus obtained from water gave 4-carboxamido-5-cyano-2-imidazolone.

EXAMPLE 12

1.08 g of diaminomaleonitrile, 1.01 g of triethylamine and 10 ml of dimethyl sulfoxide were charged into a 100 ml pressure-resistant glass tube. 1.10 g of dry ice was placed in a separate test tube which was then placed in the above pressure-resistant glass tube in such a manner that dry ice would not contact directly with the reaction mixture. The glass tube was then sealed and the reaction was conducted at room temperature for 20 hours. After completion of the reaction, the reaction mixture was worked up in the same manner as described in Example 2 to obtain 2.24 g (97% yield) of a complex of 4-carboxamido-5-cyano-2-imidazolone and dimethyl sulfoxide.

Recrystallization of the complex thus obtained from water gave 4-carboxamido-5-cyano-2-imidazolone.

While the invention has been described in detail and with reference to specific embodiments thereof, it will be apparent to one skilled in the art that various modifications and changes can be made therein without departing from the spirit and scope thereof.

What is claimed is:

1. A process for producing 4-carboxamido-5-cyano-2-imidazolone which comprises reacting diaminomaleonitrile in the presence of a basic catalyst selected from the group consisting of a trialkylamine having 1 to 4 carbon atoms in each of the alkyl moieties thereof, triethylenediamine, hexamethylenetetramine, N-methylmorpholine, and pyridine with carbon dioxide in an organic polar solvent selected from the group consisting of dimethyl sulfoxide, N,N-dimethylformamide, an alcohol having 1 to 4 carbon atoms, tetrahydrofuran, dioxane, diethyl ether, dimethoxyethane, pyridine, acetonitrile and ethyl acetate at a temperature of from about 0° C to about 60° C.

2. The process according to claim 1, wherein said reaction is conducted in the presence of a basic catalyst in an amount of from about 0.1 mole to about 1 mole per mole of said diaminomaleonitrile.

* * * * *